United States Patent [19]

Moeller et al.

[11] Patent Number: 5,616,150
[45] Date of Patent: Apr. 1, 1997

[54] ISATIN-CONTAINING FORMULATIONS FOR COLORING KERATIN-CONTAINING FIBERS

[75] Inventors: Hinrich Moeller, Monheim; Horst Hoeffkes, Duesseldorf, both of Germany

[73] Assignee: Henkel Kommanditgesellschaft auf Aktien, Duesseldorf, Germany

[21] Appl. No.: 535,261

[22] PCT Filed: Apr. 21, 1994

[86] PCT No.: PCT/EP94/01246

§ 371 Date: Oct. 30, 1995

§ 102(e) Date: Oct. 30, 1995

[87] PCT Pub. No.: WO94/24988

PCT Pub. Date: Nov. 10, 1994

[30] Foreign Application Priority Data

Apr. 30, 1993 [DE] Germany ............... 43 14 317.2

[51] Int. Cl.$^6$ ................................. A61K 7/13
[52] U.S. Cl. .................. 8/405; 8/409; 8/423; 8/574; 8/618
[58] Field of Search .................. 8/405, 406, 409, 8/407, 423, 574, 618; 548/485

[56] References Cited

U.S. PATENT DOCUMENTS

| | | | |
|---|---|---|---|
| 4,750,908 | 6/1988 | Rosenbaum et al. | 8/429 |
| 4,875,902 | 10/1989 | Grollier et al. | 8/406 |
| 4,921,503 | 5/1990 | Anderson et al. | 8/408 |
| 5,190,564 | 3/1993 | Lang et al. | 8/423 |
| 5,248,684 | 9/1993 | Suzuki et al. | 514/299 |
| 5,261,926 | 11/1993 | Lang et al. | 8/406 |
| 5,275,626 | 1/1994 | Grollier | 8/405 |
| 5,279,616 | 1/1994 | Lang et al. | 8/406 |
| 5,340,366 | 8/1994 | Lang et al. | 8/406 |

FOREIGN PATENT DOCUMENTS

| | | |
|---|---|---|
| 0359465 | 3/1990 | European Pat. Off. . |
| 0497697 | 8/1992 | European Pat. Off. . |
| 0502784 | 9/1992 | European Pat. Off. . |
| 0502783 | 9/1992 | European Pat. Off. . |
| 2716671 | 10/1978 | Germany . |
| 3635147 | 4/1987 | Germany . |

Primary Examiner—Paul Lieberman
Assistant Examiner—Caroline L. Dusheck
Attorney, Agent, or Firm—Ernest G. Szoke; Wayne C. Jaeschke; Real J. Grandmaison

[57] ABSTRACT

A composition for coloring keratin-containing fibers containing:

(a) at least one isatin derivative corresponding to formula I:

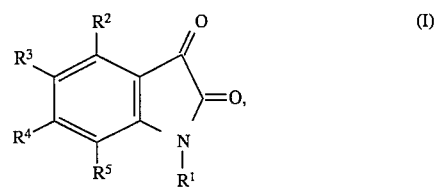

wherein $R^1$ can represent hydrogen, a $C_{1-4}$ alkyl group, a $C_{2-4}$ hydroxyalkyl group, a $C_{2-20}$ acyl group, a phenyl group, and a benzoyl group, and $R^2$, $R^3$, $R^4$ and $R^5$ independently of one another can represent hydrogen, hydroxy, halogen, nitro groups, sulfo groups, carboxyl groups, $C_{1-4}$ alkyl groups, $C_{1-4}$ alkoxy groups or $NR^6R^7$ groups and where $R^6$ and $R^7$ independently of one another represent hydrogen, $C_{1-4}$ alkyl groups or $C_{2-4}$ hydroxyalkyl groups, and wherein two adjacent groups $R^3$, $R^4$ and $R^5$ may also represent an alkylenedioxy group containing 1 to 4 carbon atoms, (b) at least one compound selected from the group consisting of: (i) primary aliphatic amines; (ii) heterocyclic or isocyclic aromatic compounds without a primary amino group; (iii) aromatic carboxylic and sulfonic acids with a primary amino group; (iv) aniline derivatives; (v) dianiline derivatives; (vi) non-aromatic unsubstituted or amino-($C_{1-4}$)-alkyl-, hydroxy-($C_{1-4}$)-alkyl-carboxyl-substituted hetero-cycles; and (vii)amino sugars; and (c) a water-containing carrier.

20 Claims, No Drawings

ISATIN-CONTAINING FORMULATIONS FOR COLORING KERATIN-CONTAINING FIBERS

BACKGROUND OF THE INVENTION

1. Field of the Invention

This invention relates to formulations for coloring keratin-containing fibers, more particularly human hair, which contain isatins and another compound. In one preferred embodiment, the formulations according to the invention additionally contain an ammonium or metal salt.

Keratin-containing fibers, for example hair, wool or furs, are generally colored either with substantive dyes or with oxidation dyes which are formed by oxidative coupling of one or more primary intermediates with one another or with one or more secondary intermediates. Although intensive colors with good fastness properties can be obtained with oxidation dyes, development of the color takes place under the effect of oxidizing agents, such as $H_2O_2$ for example, which frequently results in damage to the fibers. Although substantive dyes are applied under more moderate conditions, their disadvantage is that the colors often have unsatisfactory fastness properties.

2. Discussion of Related Art

Coloring systems based on isatin or isatin derivatives offer an alternative solution. Isatin is described in DE-OS 36 35 147 A1 as a substantive dye for coloring keratin fibers either on its own or in conjunction with quinone dyes. Unfortunately, the range of variation of the color tones obtainable is limited. In most cases, a golden color is obtained.

Another isatin-containing coloring system is described in EP 359 465 A2. In this case, the color is obtained with a ketimine (Schiff's base) produced by the reaction of an isatin with an aniline derivative. The ketimine is either applied as such to keratin fibers where it develops color or, alternatively, a mixture consisting of an isatin and an aniline derivative is applied to the fibers and initially forms the ketimine in situ, after which the color develops on the fibers.

EP 497 697 A1 describes hair coloring formulations based on isatins and aminoindoles or indolines containing a primary amino group, Schiff's based being formed in a condensation reaction.

EP 0 502 783 A1 describes hair coloring formulations containing isatins and aminopyridines or isatins and aminopyrimidines containing a primary amino group.

EP 0 502 784 A1 describes hair coloring formulations containing isatins and substituted diamines or aminophenols or isatins and (bisaryl)-alkylenediamines.

DESCRIPTION OF THE INVENTION

It has now surprisingly been found that isatins in combination with a number of other compounds, including secondary and tertiary amines, i.e. amines which are not capable of forming Schiff's bases, are suitable for coloring keratin fibers.

Examples of keratin fibers are wool, furs, skins and human hair. Although the best colors are obtained on keratin fibers, the coloring formulations according to the invention may also be used in principle for coloring other natural fibers such as, for example, cotton, jute, sisal, linen or silk; modified natural fibers such as, for example, regenerated cellulose, nitrocellulose, alkyl or hydroxyalkylcellulose or acetyl cellulose; and synthetic fibers such as, for example, polyamide, polyacrylonitrile, polyurethane and polyester fibers.

The coloring formulations described in more detail hereinafter have very good performance properties, including for example levelling power and dye absorption capacity. The colors obtained with the coloring formulations are fast to light, rubbing and washing and show high resistance to permanent-wave liquids.

The present invention relates to formulations for coloring keratin-containing fibers containing at least one isatin derivative corresponding to formula I:

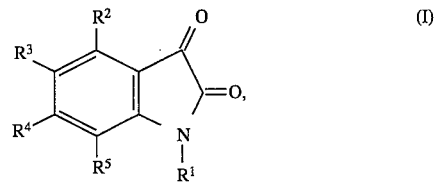

in which $R^1$ is hydrogen, a $C_{1-4}$ alkyl group, a $C_{2-4}$ hydroxyalkyl group, a $C_{2-20}$ acyl group, a phenyl group or a benzoyl group and $R^2$, $R^3$, $R^4$ and $R^5$ independently of one another represent hydrogen, hydroxy, halogen, nitro groups, sulfo groups, carboxyl groups, $C_{1-4}$ alkyl groups, $C_{1-4}$ alkoxy groups or $NR^6R^7$ groups where $R^6$ and $R^7$ independently of one another represent hydrogen, $C_{1-4}$ alkyl groups or $C_{2-4}$ hydroxyalkyl groups; two adjacent groups $R^3$, $R^4$ and $R^5$ may also represent an alkylenedioxy group containing 1 to 4 carbon atoms, at least one compound selected from the group of
a) primary aliphatic amines which contain at least one additional group $NR^8R^9$ or $OR^{10}$ in the C chain, $R^8$, $R^9$ and $R^{10}$ independently of one another representing hydrogen, $C_{1-4}$ alkyl groups, $C_{2-4}$ hydroxyalkyl groups or $C_{2-4}$-($C_{1-4}$-alkoxy)-alkyl groups,
b) heterocyclic or isocyclic aromatic compounds without a primary amino group,
c) aromatic carboxylic and sulfonic acids with a primary amino group.
d) aniline derivatives corresponding to formula II:

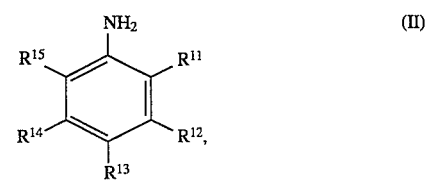

in which $R^{11}$, $R^{12}$, $R^{13}$, $R^{14}$ and $R^{15}$ represent hydrogen, $C_{1-4}$ alkyl groups, $C_{2-4}$ hydroxyalkyl groups, $C_{2-4}$-($C_{1-4}$ alkoxy)-alkyl groups or groups $NR^{16}R^{17}$ or $OR^{18}$, where $R^{16}$, $R^{17}$ and $R^{18}$ independently of one another represent hydrogen, $C_{1-4}$ alkyl groups, $C_{2-4}$ hydroxyalkyl groups or $C_{2-4}$-($C_{1-4}$ alkoxy)-alkyl groups, with the proviso that at most two of the groups $R^{11}$ to $R^{15}$ are not an $NR^{16}R^{17}$ and/or $OR^{18}$ group,
e) aniline derivatives corresponding to formula III:

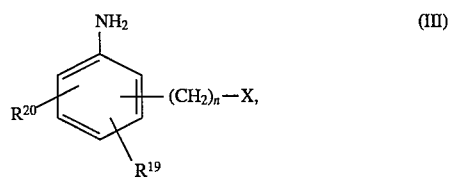

in which n is an integer of 1 to 4 and X is a hydroxy or amino group and $R^{19}$ and $R^{20}$ represent hydrogen, $C_{1-4}$ alkyl groups, $C_{2-4}$ hydroxyalkyl groups, $C_{2-4}$-($C_{1-4}$ alkoxy)-alkyl groups or groups $NR^{21}R^{22}$ or $OR^{23}$, where $R^{21}$, $R^{22}$ and $R^{23}$ independently of one another represent hydrogen, $C_{1-4}$ alkyl groups, $C_{2-4}$ hydroxyalkyl groups or $C_{2-4}$-$(C_{1-4}$ alkoxy)-alkyl groups, with the proviso that at least one of the groups $R^{19}$ and $R^{20}$ is a group $NR^{21}R^{22}$ or $OR^{23}$, f) dianiline derivatives corresponding to formula IV:

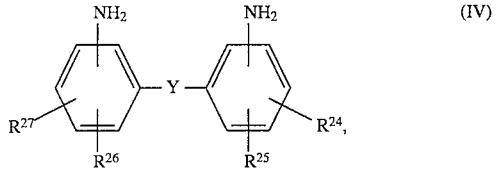

in which Y is a direct bond or a group CO, SO, O, S or $O$—$(CH_2$—Z—$CH_2$—$O)_m$, where Z is a direct bond, a group $CH_2$, CHOH or $CH_2OC_2H_4OCH_2$ and m is an integer of 1 to 4, or Y may even be a saturated or unsaturated alkylene group containing 1 to 4 carbon atoms which may optionally be substituted by OH and $R^{24}$, $R^{25}$, $R^{26}$ and $R^{27}$ represent hydrogen, $C_{1-4}$ alkyl groups, $C_{2-4}$ hydroxyalkyl groups, $C_{2-4}$-$(C_{1-4}$ alkoxy)-alkyl groups or groups $NR28R^{29}$ or $OR^{30}$, where $R^{28}$, $R^{29}$ and $R^{30}$ independently of one another represent hydrogen, $C_{1-4}$ alkyl groups, $C_{2-4}$ hydroxyalkyl groups or $C_{2-4}$-$(C_{1-4}$ alkoxy)alkyl groups, with the proviso that at least one of the groups $R^{24}$ and $R^{25}$ and one of the groups $R^{26}$ and $R^{27}$ is a group $NR^{28}R^{29}$ or $OR^{30}$, g) non-aromatic unsubstituted or amino-$(C_{1-4})$-alkyl-, hydroxy-$(C_{1-4})$-alkyl- or carboxyl-substituted heterocycles, h) amino sugars, and a water-containing carrier.

Particularly good coloring results are obtained with the formulations according to the invention when, in the isatin derivative of formula I, $R^1$ is hydrogen and $R^2$, $R^3$, $R^4$ and $R^5$ independently of one another represent hydrogen, hydroxy, halogen, methyl groups, sulfo groups or $NR^6R^7$ groups, where $R^6$ and $R^7$ represent hydrogen. The parent compound itself, isatin, is particularly preferred.

In all cases, salts of the isatin derivatives corresponding to formula I and of the compounds mentioned under a) to g) may also be used. In the case of compounds containing amino functions, the sulfates, hydrochlorides or hydrobromides, for example, may be used. In the case of compounds containing carboxy or sulfo functions, the alkali metal or ammonium salts, for example, or even inner salts may be used.

Mixtures of different isatins corresponding to formula I or salts thereof may also be used. In addition, mixtures of the compounds mentioned under a) to g) may also be used.

Preferred formulations for coloring keratin-containing fibers are those in which the aliphatic amines defined above under a) are selected from 2-aminoethanol, 2-methoxyamine, 2-ethoxyethylamine, 2-(2-aminoethoxy)-ethanol, 2-aminopropanol, 3-aminopropanol, 2,3-dihydroxypropylamine, 4-hydroxypropylamine, 2-aminopropane-1,3-diol, 2-amino-2-methyl propanol, 2-amino-2-methyl propane-1,3-diol, 2-amino-2-hydroxymethyl propane-1,3-diol, tetrahydroxypentylamines, pentahydroxyhexylamines, 1,2-diaminoethane, 1,2-diaminopropane, 1,3-diaminopropane, 1,3-diamino-2-propanol, 2-(2-aminoethylamino)-ethylamine, 2-(2-aminoethylamino)ethanol, 3-(2-aminoethylamino)-propylamine, 3-(2-aminoethylamino)-propanol, the heterocyclic or isocyclic aromatic compounds with no primary amino group defined above under b) are selected from indoline, indole, pyrrole, 3-pyrroline, pyrrolidine, 1-methyl pyrrole, 2-methyl pyrrole, 3-methyl pyrrole, 2,5-dimethyl pyrrole, pyrazole, 3-methyl pyrazole, imidazole, indoxyl acetate, tetrahydroquinoline, tetrahydroisoquinoline, 2-indole carboxylic acid, 3-indolyl acetic acid, 4-dimethyl aminopyridine, 2,6-dihydroxy-3,4-dimethyl pyridine, pyrrole-2-carboxylic acid, 2-methyl resorcinol, the aromatic carboxylic and sulfonic acids containing a primary amino group defined above under c) are selected from 2-, 3- or 4-aminobenzoic acid, 2-, 3- or 4-phenyl acetic acid, 2,3-, 2,4-, 2,5-, 3,4- or 3,5-diaminobenzoic acid, 4- or 5-aminosalicylic acid, 3-amino-4-hydroxybenzoic acid, 4-amino-3-hydroxybenzoic acid, 2-, 3- or 4-aminobenzene sulfonic acid, 4-amino-3-hydroxynaphthalene-1-sulfonic acid, 3-aminophthalic acid, 5-aminoisophthalic acid, the aniline derivatives of formula II defined above under d) are selected from 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, the aniline derivatives of formula III defined above under e) are selected from 2-(2,5-diaminophenyl)-ethanol, 2-,3-aminomethyl-4-aminophenol, 3-(2,5-diaminophenyl)propanol, 2-aminomethyl-4-aminophenol, 2-aminomethyl-5-aminophenol, 2-(2,4-diaminophenyl)-ethanol, the dianiline derivatives of formula IV defined above under f) are selected from 4,4'-diaminostilbene, 4,4'-diaminostilbene-2,2'-disulfonic acid, 4,4'-diaminodiphenyl methane, 4,4'-diaminodiphenyl sulfide, 4,4'-diaminodiphenyl sulfoxide, 4,4'-diaminobenzophenone, 4,4'-diaminobenzodiphenyl ether, 3,3',4,4'-tetraaminodiphenyl, 3,3',4,4'-tetraaminobenzophenone, 1,3-bis-(2,4-diaminophenoxy)-propane, 1,8-bis- (2,5-diaminophenoxy) -3,6-dioxaoctane, the non-aromatic heterocycles defined above under g) are selected from piperidine, piperazine, 1-(2-aminooctyl)-piperazine, 1-(2-hydroxyethyl)-piperazine, 3-pyrroline, pyrrolidine, thiazolidine, thiazolidine-4-carboxylic acid, piperidine-2-carboxylic acid, piperidine-3-carboxylic acid, piperidine-4-carboxylic acid, the amino sugars h) are selected from D-glucosamine and D-galactosamine.

If certain ammonium or metal salts are added to the coloring formulations according to the invention, particularly intensive colors are obtained after only a short time at relatively low temperatures.

Accordingly, the present invention also relates to formulations for coloring keratin-containing fibers which contain at least one salt selected from the group consisting of ammonium, lithium, sodium, potassium, magnesium, calcium, strontium, barium, aluminium, titanium, manganese, iron, cobalt, nickel, copper, silver, zinc, lanthanum, cerium, praseodymium, neodymium and gadolinium salts.

Particularly suitable salts are ammonium carbonate, ammonium acetate, sodium acetate, lithium acetate, potassium acetate, sodium glycolate, sodium lactate, calcium gluconate. The coloring formulations according to the invention give intensive colors with a wide range of tones after only 30 minutes at temperatures of 35° C. Accordingly, they are particularly suitable for coloring human hair because a temperature of 35° C. can be reached on the head without any need for an additional heat source.

The present invention also relates to hair coloring formulations containing at least one isatin corresponding to formula I in a quantity of 0.3 to 65 mmoles and preferably 6 to 20 mmoles, at least one primary aliphatic amine of the type defined above under a) in a quantity of 0.3 to 65 mmoles and preferably 6 to 20 mmoles, based on 100 g of the coloring formulation as a whole, and a water-containing carrier.

The present invention also relates to hair coloring formulations containing at least one isatin corresponding to formula I in a quantity of 0.3 to 65 mmoles and preferably 6 to 20 mmoles, at least one heterocyclic or isocyclic aromatic compound with no primary amino group of the type defined above under b) in a quantity of 0.3 to 65 mmoles and preferably 6 to 20 mmoles, based on 100 g of the coloring formulation as a whole, and a water-containing carrier.

The present invention also relates to hair coloring formulations containing at least one isatin corresponding to formula I in a quantity of 0.3 to 65 mmoles and preferably 6 to 20 mmoles, at least one aromatic carboxylic or sulfonic acid with a primary amino group of the type defined above under c) in a quantity of 0.3 to 65 mmoles and preferably 6 to 20 mmoles, based on 100 g of the coloring formulation as a whole, and a water-containing carrier.

The present invention also relates to hair coloring formulations containing at least one isatin corresponding to formula I in a quantity of 0.3 to 65 mmoles and preferably 6 to 20 mmoles, at least one aniline derivative corresponding to formula II of the type defined above under d) in a quantity of 0.3 to 65 mmoles and preferably 6 to 20 mmoles, based on 100 g of the coloring formulation as a whole, and a water-containing carrier.

The present invention also relates to hair coloring formulations containing at least one isatin corresponding to formula I in a quantity of 0.3 to 65 mmoles and preferably 6 to 20 mmoles, at least one aniline derivative corresponding to formula III of the type defined above under e) in a quantity of 0.3 to 65 mmoles and preferably 6 to 20 mmoles, based on 100 g of the coloring formulation as a whole, and a water-containing carrier.

The present invention also relates to hair coloring formulations containing at least one isatin corresponding to formula I in a quantity of 0.3 to 65 mmoles and preferably 6 to 20 m moles, at least one dianiline derivative corresponding to formula IV of the type defined above under f) in a quantity of 0.3 to 65 mmoles and preferably 6 to 20 mmoles, based on 100 g of the coloring formulation as a whole, and a water-containing carrier.

The present invention also relates to hair coloring formulations containing isatins corresponding to formula I in a quantity of 0.3 to 65 mmoles and preferably 6 to 20 mmoles, at least one non-aromatic heterocyclic compound of the type defined above under g) in a quantity of 0.3 to 65 mmoles and preferably 6 to 20 mmoles, based on 100 g of the coloring formulation as a whole, and a water-containing carrier.

The present invention also relates to hair coloring formulations containing isatins corresponding to formula I in a quantity of 0.3 to 65 mmoles and preferably 6 to 20 mmoles, an amino sugar h) in a quantity of 0.3 to 65 mmoles and preferably 6 to 20 mmoles, based on 100 g of the coloring formulation as a whole, and a water-containing carrier.

Water-containing carriers are, for example, creams, emulsions, gels or even surfactant-containing foaming solutions, such as shampoos for example, or other preparations suitable for application to the hair. The water-containing cosmetic carrier typically contains wetting agents and emulsifiers, such as anionic, nonionic or ampholytic surfactants, for example fatty alcohol sulfates, alkane sulfonates, α-olefin sulfonates, fatty alcohol polyglycol ether sulfates, alkyl glycosides, ethylene oxide adducts with fatty alcohols, with fatty acids, with alkylphenols, with sorbitan fatty acid esters, with fatty acid partial glycerides and fatty acid alkanolamides; thickeners, for example fatty alcohols, fatty acids, paraffin oils, fatty acid esters and other fatty components in emulsified form; water-soluble polymeric thickeners, such as natural gums, for example gum arabic, karaya gum, guar gum, carob bean flour, linseed gums and pectin, biosynthetic gums, for example xanthan gum and dextrans, synthetic gums, for example agar agar and algin, starch fractions and derivatives, such as amylose, amylopectin and dextrins, modified cellulose molecules, for example methyl cellulose, hydroxyalkyl cellulose and carboxymethyl cellulose, clays, for example bentonite, or fully synthetic hydrocolloids, for example polyvinyl alcohol or polyvinyl pyrrolidone, hair-care additives, for example water-soluble cationic polymers, anionic polymers, nonionic polymers, amphoteric or zwitterionic polymers, pantothenic acid, vitamins, plant extracts or cholesterol, pH regulators, complexing agents and perfume oils and also reducing agents for stabilizing the ingredients, for example ascorbic acid. Finally, dyes may also be present to color the cosmetic preparations.

The hair coloring formulations are particularly preferred when they additionally contain a salt selected from the group consisting of ammonium, lithium, sodium, potassium, magnesium, calcium, strontium, barium, aluminium, titanium, manganese, iron, cobalt, nickel, copper, silver, zinc, lanthanum, cerium, praseodymium, neodymium or gadolinium salts in a quantity of 0.3 to 65 mmoles and preferably 2 to 15 mmoles, based on 100 g of the coloring formulation as a whole.

The pH value of the formulation is either in the range of the pH value spontaneously established for the particular compound a) to h) or, alternatively, may be adjusted to a value of 3 to 10. The pH value is preferably at around 6. It is important in this connection to bear in mind the fact that, in some cases, the color tone is pH-dependent.

For coloring hair, the hair coloring formulations according to the invention are applied to the hair in the form of a water-containing cosmetic carrier in a quantity of 100 g, left thereon for about 30 minutes and then rinsed out or washed out with a commercial hair shampoo.

There are several possibilities for packaging the hair coloring formulations according to the invention.

If the hair coloring formulation contains only the two components isatin derivative and compound a) to h), there are two possibilities for packaging, i.e. either both components in one container or both components in separate containers. With packaging in separate containers, the two components may be successively applied to the hair or, alternatively, may be mixed together just before application.

If the coloring formulation contains the three components isatin derivative, compound a) to h) and ammonium or metal salt, there are three possibilities for packaging, namely in one, in two or in three containers.

In the following illustration, I stands for isatin derivative, V for compound a) to h) and S salt:
1) Packaging in one container: I+A+S
2) Packaging in two containers:
   a) container 1: I+S, container 2: V
   b) container 1: V+S, container 2: I
   c) container 1: V+I, container 2: S In each of the three packaging variants 2a), 2b) and 2c), the components may be mixed together before application to the hair or may be successively applied to the hair. Where the components are separately applied to the hair, there are two possibilities, namely: first the contents of container 1 and then the contents of container 2 are applied to the hair or first the contents of container 2 and then the contents of container 1 are applied.

3) Packaging in three containers:
   container 1: I, container 2: V, container 3: S.

The three components I, V and S may be successively applied to the hair in any order although they may also be mixed together just before application. Another possibility is initially to mix only two of the three components I, V and S together, to apply the resulting mixture to the hair and only then to add the third component.

EXAMPLES

EXAMPLE 1

Preparation of a coloring solution:

A suspension of 10 mmoles of isatin and 1 mmole of one of the components listed under a) to h) in claim 1 in 100 ml of water was prepared. The particularly preferred compositions according to the invention additionally contained 10 mmoles of ammonium or metal salt. The suspension was heated to boiling temperature and filtered after cooling. The pH value was subsequently adjusted to 6 with hydrochloric acid.

90% Grey, but non-pretreated human hair were placed in this coloring solution for 30 minutes at 35° C. The particular coloring temperatures, coloring times, color tones and depth of color are shown in Table 1.

Depth of color was evaluated on the following scale:
−: Very pale color, if any
(+): Weak intensity
+: Medium intensity
+(+): Medium to strong intensity
++: Strong intensity
++(+): Strong to very strong intensity
+++: Very strong intensity

TABLE 1

| Coloring with isatin | | | |
|---|---|---|---|
| Compound according to claim 1 a) to h) | Salt (10 mmoles) | Color tone | Depth of color |
| — | NaAc | Yellow | (+) |
| Ethanolamine | NaAc | Copper red | +(+) |
| 1,2-Diaminoethane | NaAc | Red-brown | ++ |
| 2-Indole carboxylic acid | NaAc | Yellow-orange | (+) |
| Pyrrole | NaAc | Black | +++ |
| 4-Dimethylamino-pyridine | NaAc | Orange-yellow | + |
| Indoxyl acetate | NaAc | Light copper | +(+) |
| Pyrazole | NaAc | Orange-yellow | (+) |
| 2,3-Dimethyl pyrrole | NaAc | Yellow-orange | +(+) |
| Indoline | NaAc | Copper | + |
| 2-Pyrrole carboxylic acid | NaAc | Orange-brown | +(+) |
| Thiophene | NaAc | Yellow | + |
| Furan | NaAc | Yellow | + |
| Thiophene-2-acetic acid | NaAc | Deep yellow | + |
| N-Methyl pyrrole | NaAc | Yellow | + |
| 3-Indolyl acetic acid | NaAc | Orange-yellow | (+) |
| 2-Pyrrole carboxylic acid | NaAc | Orange-brown | +(+) |
| Pyrrole | (NH$_4$)$_2$CO$_3$ | Olive-green | ++ |
| Pyrrole | LiAc | Olive-yellow | ++ |
| Pyrrole | Na glycolate | Olive-green | +(+) |
| 2,6-Dihydroxy-3,4-dimethyl pyridine | NaAc | Yellow-brown | ++ |
| 2-Methyl resorcinol | NaAc | Deep yellow | ++(+) |
| 4-Aminobenzoic acid | NaAc | Orange-yellow | +(+) |
| 3,4-Diaminobenzoic acid | NaAc | Pure yellow | + |
| 3,4-Diaminobenzoic acid | — | Yellow | (+) |

TABLE 1-continued

| Coloring with isatin | | | |
|---|---|---|---|
| Compound according to claim 1 a) to h) | Salt (10 mmoles) | Color tone | Depth of color |
| 3,4-Diaminobenzoic acid | Na glycolate | Orange-yellow | + |
| 3,5-Diaminobenzoic acid | NaAc | Dark yellow | ++ |
| 1,2,4,5-Tetraamino-benzene.4HCl | NaAc | Red-brown (chestnut) | ++(+) |
| 2-(2,5-Diaminophen-yl)-ethanol | NaAc | Dark red | ++(+) |
| 3-Aminomethyl-4-hy-oxyaniline | NaAc | Brown-orange | ++ |
| 4,4'-Diaminostilbene.2HCl | NaAc | Brown-yellow | ++ |
| 1,8-Bis-(2,5-diamino-phenoxy)-3,6-dioxa-octane | NaAc | Dark red-black | ++ |
| 1,3-Bis-(2,4-diamino-phenoxy)-propane.4HCl | NaAc | Deep brown | ++ |
| 1-(2-Aminoethyl)-piperazine | NaAc | Grey-orange | + |
| D-Glucosamine | NaAc | Copper | +(+) |

EXAMPLE 2

The coloring solution was prepared as in Example 1, but with isatin-5-sulfonic acid instead of isatin.

TABLE 2

| Coloring with isatin-5-sulfonic acid | | | |
|---|---|---|---|
| Compound according to claim 1 a) to h) | Salt (10 mmoles) | Color tone | Depth of color |
| 2,4,5,6-Tetraamino-pyrimidine | NaAc | Copper | ++ |
| 1,2,4,5-Tetraamino-benzene | NaAc | Olive-brown | ++ |
| 1,8-Bis-(2,5-diamino-phenoxy)-3,6-dioxa-octane | NaAc | Red-violet | ++ |
| 2-(2,5-Diaminophen-yl)-ethanol | NaAc | Dark violet-red | +++ |
| 3,4-Diaminobenzoic acid | NaAc | Yellow | +(+) |
| — | NaAc | Yellow | + |
| — | NaAc, ZnCl$_2$ | Yellow | +(+) |

We claim:
1. A composition for coloring keratin-containing fibers comprising:

(a) from 0.3 to 65 mmoles of at least one isatin derivative corresponding to formula I:

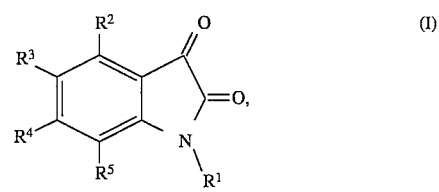

wherein $R^1$ represents hydrogen, a $C_{1-4}$ alkyl group, a $C_{2-4}$ hydroxyalkyl group, a $C_{2-20}$ acyl group, a phenyl group, and a benzoyl group, and $R^2$, $R^3$, $R^4$ and $R^5$ independently of one another represent hydrogen, hydroxy, halogen, nitro groups, sulfo groups, carboxyl groups, $C_{1-4}$ alkyl groups, $C_{1-4}$ alkoxy groups or NR⁶R⁷ groups wherein R⁶ and R⁷ independently of one another represent hydrogen, $C_{1-4}$ alkyl groups or $C_{2-4}$ hydroxyalkyl groups, and wherein two adjacent groups $R^3$, $R^4$ and $R^5$ may also represent an alkylenedioxy group containing 1 to 4 carbon atoms, (b) from 0.3 to 65 mmoles of at least one compound selected from the group consisting of: (i) primary aliphatic amines selected from the group consisting of 2-methoxyamine, 2-ethoxyethylamine, 2-(2-aminoethoxy)-ethanol, 2,3-dihydroxypropylamine, 2-aminopropane-1,3-diol, 2-amino-2-methyl propane-1,3-diol, 2-amino-2-hydroxymethyl propane-1,3-diol, tetrahydroxy-pentylamines, pentahydroxyhexylamines, 1,2-diaminoethane, 1,2-diaminopropane, 1,3-diaminopropane, 1,3-diamino-2-propanol, 2-(2-aminoethylamino)-ethylamine, 2-(2-aminoethylamino)-ethanol, 3-(2-aminoethylamino)-propylamine, 3-(2-aminoethylamino)-propanol, and mixtures thereof; (ii) indoline, indole, pyrrole, 1-methyl pyrrole, 2-methyl pyrrole, 3-methyl pyrrole, 2,5-ethyl pyrrole, pyrazole, 3-methyl pyrazole, imidazole, indoxyl acetate, tetrahydroquinoline, tetrahydroisoquinoline, 2-indole carboxylic acid, 3-indolyl acetic acid, 4-dimethylaminopyridine, 2,6-dihydroxy-3,4-dimethyl pyridine, pyrrole-2-carboxylic acid, 2-methyl resorcinol, and mixtures thereof; (iii) aromatic carboxylic and sulfonic acids with a primary amino group; (iv) aniline derivatives corresponding to formula III;

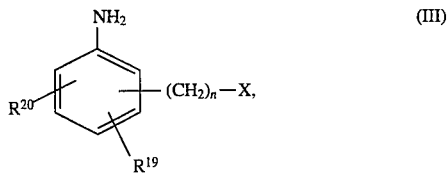

(III)

wherein n is an integer from 1 to 4, X is a hydroxy or amino group and $R^{19}$ and $R^{20}$ represent hydrogen, $C_{1-4}$ alkyl groups, $C_{2-4}$ hydroxyalkyl groups, $C_{2-4}$-($C_{1-4}$ alkoxy)-alkyl groups, $NR^{21}R^{22}$ groups or $OR^{23}$ groups, wherein $R^{21}$, $R^{22}$ and $R^{23}$ independently of one another represent hydrogen, $C_{1-4}$ alkyl groups, $C_{2-4}$ hydroxyalkyl groups or $C_{2-4}$-($C_{1-4}$ alkoxy)-alkyl groups, with the proviso that at least one of the groups $R^{19}$ and $R^{20}$ is a group $NR^{21}R^{22}$ or $OR^{23}$; (v) dianiline derivatives corresponding to formula IV:

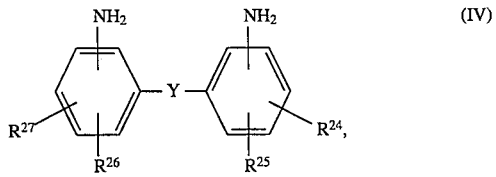

(IV)

wherein Y represents a direct bond, CO, SO, O, S or O—(CH₂—Z—CH₂—O)ₘ, wherein Z represents a direct bond, CH₂, CHOH or CH₂OC₂H₄OCH₂ and m is an integer from 1 to 4, a saturated alkylene group having 1–4 carbon atoms which may be substituted with an OH group, an unsaturated alkylene group having 1 to 4 carbon atoms which may be substituted with an OH group, and wherein $R^{24}$, $R^{25}$, $R^{26}$ and $R^{27}$ represent hydrogen, $C_{1-4}$ alkyl groups, $C_{2-4}$ hydroxyalkyl groups, $C_{2-4}$-($C_{1-4}$ alkoxy)-alkyl groups, $NR^{28}R^{29}$ groups or $OR^{30}$ groups, wherein $R^{28}$, $R^{29}$ and $R^{30}$ independently of one another represent hydrogen, $C_{1-4}$ alkyl groups, $C_{2-4}$ hydroxyalkyl groups or $C_{2-4}$-($C_{1-4}$ alkoxy)-alkyl groups, with the proviso that at least one of the groups $R^{24}$ and $R^{25}$ and one of the groups $R^{26}$ and $R^{27}$ is a $NR^{28}R^{29}$ group or $OR^{30}$ group; (vi) non-aromatic unsubstituted or amino-($C_{1-4}$)-alkyl-, hydroxy-($C_{1-4}$)-alkyl- or carboxyl-substituted heterocycles; and (vii) amino sugars, all amounts being based on 100 grams of said composition; and (c) a water-containing carrier.

2. The composition of claim 1 wherein in formula I, $R^1$ is hydrogen and $R^2$, $R^3$, $R^4$ and $R^5$ independently of one another represent hydrogen, hydroxy, halogen, methyl, sulfo groups or NR⁶R⁷ groups, wherein R⁶ and R⁷ are hydrogen.

3. The composition of claim 1 wherein in formula I, $R^1$, $R^2$, $R^3$, $R^4$ and $R^5$ are all hydrogen.

4. The composition of claim 1 wherein said component (b)(iii) is selected from the group consisting of 2-, 3- and 4-aminobenzoic acid, 2-, 3- and 4-phenyl acetic acid, 2,3-, 2,4-, 2,5-, 3,4- and 3,5-diaminobenzoic acid, 4- or 5-aminosalicylic acid, 3-amino-4hydroxybenzoic acid, 4-amino-3-hydroxybenzoic acid, 2-, 3- and 4-aminobenzene sulfonic acid, 4-amino-3-hydroxynaphthalene-1-sulfonic acid, 3-aminophthalic acid, 5-aminoisophthalic acid, and mixtures thereof.

5. The composition of claim 1 wherein said component (b)(iv) is selected from the group consisting of 2-(2,5-diaminophenyl)-ethanol, 2-,3-aminomethyl-4-aminophenol, 3-(2,5-diaminophenyl)-propanol, 2-aminomethyl-4-aminophenol, 2-aminomethyl-5-aminophenol, 2-(2,4-diaminophenyl)-ethanol, and mixtures thereof.

6. The composition of claim 1 wherein said component (b)(v) is selected from the group consisting of 4,4'-diaminostilbene, 4,4'-diaminostilbene-2,2'-disulfonic acid, sodium salt, 4,4'-diaminodiphenyl methane, 4,4'-diaminodiphenyl sulfide, 4,4'-diaminodiphenyl sulfoxide, 4,4'-diaminodiphenylamine, 4,4'-diaminobenzophenone, 4,4'-diaminobenzodiphenyl ether, 3,3',4,4'-tetraaminodiphenyl, 3,3',4,4'-tetraaminobenzophenone, 1,3-bis-(2,4-diaminophenoxy)-propane, 1,8-bis-(2,5-diaminophenoxy)-3,6-dioxaoctane, and mixtures thereof.

7. The composition of claim 1 wherein said component (b)(vi) is selected from the group consisting of piperidine, piperazine, 1-(2-aminooctyl)-piperazine, 1-(2-hydroxyethyl)-piperazine, 3-pyrroline, pyrrolidine, thiazolidine, thiazolidine-4-carboxylic acid, piperidine-2-carboxylic acid, piperidine-3-carboxylic acid, piperidine-4-carboxylic acid, and mixtures thereof.

8. The composition of claim 1 wherein said component (b)(vii) is selected from the group consisting of D-glucosamine, D-galactosamine, and mixtures thereof.

9. The composition of claim 1 further containing a salt selected from the group consisting of ammonium carbonate, ammonium acetate, sodium acetate, lithium acetate, potassium acetate, sodium glycolate, sodium lactate, calcium gluconate, and mixtures thereof.

10. The composition of claim 9 wherein said salt is present in an amount of from 0.3 to 65 mmoles, based on 100 grams total of said composition.

11. A process for coloring keratin-containing fibers comprising contacting said fibers with a composition comprising:

(a) from 0.3 to 65 mmoles of at least one isatin derivative corresponding to formula I:

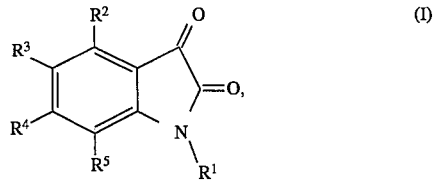

(I)

wherein $R^1$ represents hydrogen, a $C_{1-4}$ alkyl group, a $C_{2-4}$ hydroxyalkyl group, a $C_{2-20}$ acyl group, a phenyl group, and a benzoyl group, and $R^2$, $R^3$, $R^4$ and $R^5$ independently of one another represent hydrogen, hydroxy, halogen, nitro groups, sulfo groups, carboxyl groups, $C_{1-4}$ alkyl groups, $C_{1-4}$ alkoxy groups or $NR^6R^7$ groups wherein $R^6$ and $R^7$ independently of one another represent hydrogen, $C_{1-4}$ alkyl groups or $C_{2-4}$ hydroxyalkyl groups, and wherein two adjacent groups $R^3$, $R^4$ and $R^5$ may also represent an alkylenedioxy group containing 1 to 4 carbon atoms, (b) from 0.3 to 65 mmoles of at least one compound selected from the group consisting of: (i) primary aliphatic amines selected from the group consisting of 2-methoxyamine, 2-ethoxyethylamine, 2- (2-aminoethoxy) -ethanol, 2,3-dihydroxypropylamine, 2-aminopropane-1,3-diol, 2-amino-2-methyl propane-1,3-diol, 2-amino-2-hydroxymethyl propane-1,3-diol, tetrahydroxy-pentylamines, pentahydroxyhexylamines, 1,2-diaminoethane, 1,2 -diaminopropane, 1,3-diaminopropane, 1,3-diamino-2-propanol, 2- (2-aminoethylamino) -ethylamine, 2- (2-aminoethylamino) -ethanol, 3- (2-aminoethylamino) -propylamine, 3-(2-aminoethylamino)-propanol, and mixtures thereof; (ii) indoline, indole, pyrrole, 1-methyl pyrrole, 2-methylpyrrole, 3-methyl pyrrole, 2,5-dimethyl pyrrole, pyrazole, 3-methyl pyrazole, imidazole, indoxyl acetate, tetrahydroaquinoline, tetrahydroisoquinoline, 2-indole carboxylic acid, 3-indolyl acetic acid, 4-dimethyl aminopyridine, 2,6-dihydroxy-3,4-dimethyl pyridine, pyrrole-2-carboxylic acid, 2-methyl resorcinol, and mixtures thereof; (iii) aromatic carboxylic and sulfonic acids with a primary amino group; (v) aniline derivatives corresponding to formula III:

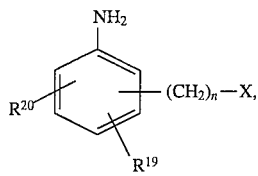

(III)

wherein n is an integer from 1 to 4, X is a hydroxy or amino group and $R^{19}$ and $R^{20}$ represent hydrogen, $C_{1-4}$ alkyl groups, $C_{2-4}$ hydroxyalkyl groups, $C_{2-4}$-($C_{1-4}$ alkoxy)-alkyl groups, $NR^{21}R^{22}$ groups or $OR^{23}$ groups, wherein $R^{21}$, $R^{22}$ and $R^{23}$ independently of one another represent hydrogen, $C_{1-4}$ alkyl groups, $C_{2-4}$ hydroxyalkyl groups or $C_{2-4}$-($C_{1-4}$ alkoxy)-alkyl groups, with the proviso that at least one of the groups $R^{19}$ and $R^{20}$ is a group $NR^{21}R^{22}$ or $OR^{23}$; (v) dianiline derivatives corresponding to formula IV:

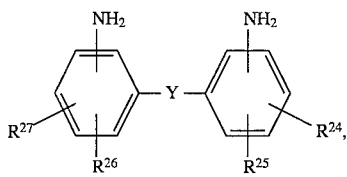

(IV)

wherein Y represents a direct bond, CO, SO, O, S or O—($CH_2$—Z—$CH_2$—O)$_m$, wherein Z represents a direct bond, $CH_2$, CHOH or $CH_2OC_2H_4OCH_2$ and m is an integer from 1 to 4, a saturated alkylene group having 1–4 carbon atoms which may be substituted with an OH group, an unsaturated alkylene group having 1 to 4 carbon atoms which may be substituted with an OH group, and wherein $R^{24}$, $R^{25}$, $R^{26}$ and $R^{27}$ represent hydrogen, $C_{1-4}$ alkyl groups, $C_{2-4}$ hydroxyalkyl groups, $C_{2-4}$-($C_{1-4}$ alkoxy)-alkyl groups, $NR^{25}R^{28}$ groups or $OR^{30}$ groups, wherein $R^{28}$, $R^{29}$ and $R^{30}$ independently of one another represent hydrogen, $C_{1-4}$ alkyl groups, $C_{2-4}$hydroxyalkyl groups or $C_{2-4}$-($C_{1-4}$ alkoxy)-alkyl groups, with the proviso that at least one of the groups $R^{24}$ and $R^{25}$ and one of the groups $R^{26}$ and $R^{27}$ is a $NR^{28}R^{29}$ group or $OR^{30}$ group; (vi) non-aromatic unsubstituted or amino-($C_{1-4}$)-alkyl-, hydroxy-($C_{1-4}$)-alkyl- or carboxyl-substituted heterocycles; and (vii) amino sugars, all amounts being based on 100 grams of said composition; and (c) a water-containing carrier.

12. The process of claim 11 wherein in formula I, $R^1$ is hydrogen and $R^2$, $R^3$, $R^4$ and $R^5$ independently of one another represent hydrogen, hydroxy, halogen, methyl, sulfo groups or $NR^6R^7$ groups, wherein $R^6$ and $R^7$ are hydrogen.

13. The process of claim 11 wherein in formula I, $R^1$, $R^2$, $R^3$, $R^4$ and $R^5$ are all hydrogen.

14. The process of claim 11 wherein said component (b)(iii) is selected from the group consisting of 2-, 3- and 4-aminobenzoic acid, 2-, 3- and 4-phenyl acetic acid, 2,3-, 2,4-, 2,5-, 3,4- and 3,5-diaminobenzoic acid, 4- or 5-aminosalicylic acid, 3-amino-4-hydroxybenzoic acid, 4-amino-3-hydroxybenzoic acid, 2-, 3- and 4-aminobenzene sulfonic acid, 4-amino-3-hydroxynaphthalene-1-sulfonic acid, 3-aminophthalic acid, 5-aminoisophthalic acid, and mixtures thereof.

15. The process of claim 11 wherein said component (b)(iv) is selected from the group consisting of 2-(2,5-diaminophenyl)-ethanol, 2-,3-aminomethyl-4-aminophenol, 3-(2,5-diaminophenyl)-propanol, 2-aminomethyl-4-aminophenol, 2-aminomethyl-5-aminophenol, 2-(2,4-diaminophenyl)-ethanol, and mixtures thereof.

16. The process of claim 11 wherein said component (b)(v) is selected from the group consisting of 4,4'-diaminostilbene, 4,4'-diaminostilbene-2,2'-disulfonic acid, sodium salt, 4,4'-diaminodiphenyl methane, 4,4'-diaminodiphenyl sulfide, 4,4'-diaminodiphenyl sulfoxide, 4,4'-diaminobenzophenone, 4,4'-diaminobenzophenone, 4,4'-diaminobenzodiphenyl ether, 3,3',4,4'-tetraaminodiphenyl, 3,3',4,4'-tetraaminobenzophenone, 1,3-bis-(2,4-diaminophenoxy)-propane, 1,8-bis-(2,5-diaminophenoxy)-3,6-dioxaoctane, and mixtures thereof.

17. The process of claim 11 wherein said component (b)(vi) is selected from the group consisting of piperidine, piperazine, 1-(2-aminooctyl)-piperazine, 1-(2-hydroxyethyl)-piperazine, 3-pyrroline, pyrrolidine, thiazolidine, thiazolidine-4-carboxylic acid, piperidine-2-carboxylic acid, piperidine-3-carboxylic acid, piperidine-4-carboxylic acid, and mixtures thereof.

18. The process of claim 11 wherein said component (b)(vii) is selected from the group consisting of D-glucosamine, D-galactosamine, and mixtures thereof.

19. The process of claim 11 wherein said composition further contains a salt selected from the group consisting of ammonium carbonate, ammonium acetate, sodium acetate, lithium acetate, potassium acetate, sodium glycolate, sodium lactate, calcium gluconate, and mixtures thereof.

20. The process of claim 19 wherein said salt is present in said composition in an amount of from 0.3 to 65 mmoles, based on 100 grams total of said composition.

* * * * *